US010433540B2

(12) United States Patent
Mohanty et al.

(10) Patent No.: US 10,433,540 B2
(45) Date of Patent: Oct. 8, 2019

(54) CAPILLARY ASSISTED VITRIFICATION PROCESSES AND DEVICES

(71) Applicant: Somnio Global Holdings, LLC, Novi, MI (US)

(72) Inventors: Pravansu S. Mohanty, Canton, MI (US); Nilay Chakraborty, Troy, MI (US)

(73) Assignee: Somnio Global Holdings, LLC, Novi, MI (US)

( * ) Notice: Subject to any disclaimer, the term of this patent is extended or adjusted under 35 U.S.C. 154(b) by 85 days.

(21) Appl. No.: 15/317,256

(22) PCT Filed: Jun. 9, 2015

(86) PCT No.: PCT/US2015/034887
§ 371 (c)(1),
(2) Date: Dec. 8, 2016

(87) PCT Pub. No.: WO2015/191570
PCT Pub. Date: Dec. 17, 2015

(65) Prior Publication Data
US 2017/0135336 A1 May 18, 2017

Related U.S. Application Data

(60) Provisional application No. 62/009,562, filed on Jun. 9, 2014.

(51) Int. Cl.
*A01N 1/02* (2006.01)
*C12M 1/00* (2006.01)

(52) U.S. Cl.
CPC ......... *A01N 1/0284* (2013.01); *A01N 1/0242* (2013.01); *A01N 1/0252* (2013.01);
(Continued)

(58) Field of Classification Search
CPC .............................. C12M 47/14; A01N 1/0268
See application file for complete search history.

(56) References Cited

U.S. PATENT DOCUMENTS 3,732,627 A * 5/1973 Wertheim ................. F26B 5/16
34/337
6,509,146 B1 1/2003 Bronshtein
(Continued)

FOREIGN PATENT DOCUMENTS

| WO | 2013026160 A1 | 2/2013 | |
|---|---|---|---|
| WO | WO-2013/026160 | 2/2013 | |
| WO | WO-2013026160 A1 * | 2/2013 | ............... F26B 5/16 |

OTHER PUBLICATIONS

Extended European Search Report dated Jan. 22, 2018 for corresponding EP Application N. 15806082.2.
(Continued)

*Primary Examiner* — William H. Beisner
(74) *Attorney, Agent, or Firm* — Dinsmore & Shohl LLP; Weston R. Gould

(57) ABSTRACT

Disclosed are devices and methods for non-cryogenic vitrification of biological materials that include the steps of providing one or more capillary channels of which a first opening is operably in contact with a moisture containing vitrification mixture made of a biological material and a vitrification agent. The capillary absorbs and transports the moisture to the second opening through capillary action, and the moisture is subsequently evaporated into a surrounding low humidity atmosphere until the vitrification mixture enters into a vitrified state.

9 Claims, 17 Drawing Sheets

(52) U.S. Cl.
CPC ......... *A01N 1/0263* (2013.01); *A01N 1/0278* (2013.01); *C12M 47/14* (2013.01)

(56) References Cited

U.S. PATENT DOCUMENTS

| | | |
|---|---|---|
| 8,821,437 B2 | 9/2014 | de Costa et al. |
| 8,900,856 B2 | 12/2014 | Muller-Cohn et al. |
| 2004/0081588 A1 | 4/2004 | Hammerstedt et al. |
| 2006/0177426 A1 | 8/2006 | Gibson et al. |
| 2011/0165553 A1* | 7/2011 | Elliott ................. A01N 1/02 435/1.1 |
| 2013/0260452 A1 | 10/2013 | Toner et al. |

OTHER PUBLICATIONS

Less, Rebekah et al, "Isothermal vitrification methodology development for non-cryogenic storage of archival human sera," Cryobiology 66 (2013) 176-185.
Loi, P. et al, "Towards storage of cells and gametes in dry form," Trends in Biotechnology, Dec. 2013, vol. 31, No. 12, pp. 688-695.
Puhlev, Iskren et al, "Desiccation Tolerance in Human Cells," Cryobiology, 42, 207-217 (2001).

* cited by examiner

CAPILLARY ASSISTED VITRIFICATION PROCESSES AND DEVICES

CROSS REFERENCE TO RELATED APPLICATIONS

This application depends from and claims priority to U.S. Provisional Application No. 62/009,562 filed Jun. 9, 2014, the entire contents of which are incorporated herein by reference.

FIELD

One aspect of the present invention relates to non-cryogenic vitrification of biological materials, in particular biological materials vitrified in a vitrification medium by capillary assisted fast drying.

BACKGROUND

Vitrification is the process of direct transition from a liquid to an amorphous glassy state and is often utilized to preserve biological materials by cooling them to cryogenic temperatures at high cooling rates. At cryogenic temperatures, vitrification technique avoids the damaging effects of ice crystals, which are known to form during conventional cryopreservation using slow cooling rates. However, in order to avoid ice-nucleation during cooling, extremely high and potentially toxic concentrations (6-8M) of cryoprotectants (CPAs) are required. Among the most commonly used CPAs are dimethyl sulfoxide (DMSO), glycerol, ethylene glycol (EG) and 1,2-propanediol (PROH). As a result, multiple steps and complex elaborate protocols are required to toad and unload CPAs into cells. Therefore, alternative approaches to achieve vitrification without the need to expose biologics to high concentrations of CPA at non-cryogenic temperature have been sought over the years.

It is known that in order to achieve cryogenic vitrification at lower CPA concentrations, ultra-fast heat transfer rates are required. Heat transfer rates can be increased by reducing the sample volume and/or by increasing the cooling rate. A number of techniques have been utilized to increase the cooling rate such as employing thin straws or ultra-thin films to minimize the volume to be vitrified. Patent application US 2013/0157250 A1, published Jun. 20, 2013 discloses a method for cryogenic vitrification of human spermatozoa in low CPA concentration employing a thin straw. More recently, taking advantage of the high thermal conductivity of quartz crystal (QC) capillaries, patent application US 2013/0260452 A, published Oct. 3, 2013 in which N. Chakraborty is a common inventor, discloses a method for vitrification of mammalian cells in low CPA concentration medium at ultra-rapid cooling rates.

Anhydrous vitrification at ambient temperatures may also be an alternative strategy for preserving biological materials. In nature, a wide variety of organisms can survive extreme dehydration which correlates in many cases with the accumulation of large amounts (as much as 20% of their dry weight) of glass forming sugars such as trehalose and sucrose in intracellular space. Such "glass forming" sugars need to be present on both sides of the plasma membrane to provide protection against the damaging effects of desiccation. Desiccation techniques dramatically limit or arrests the material's biochemical processes in a glassy matrix. Despite the success in vitrifying many biological materials such as proteins by anhydrous vitrification, broader applications to cellular materials still requires one to increase the desiccation tolerance of the cells.

Methods to enhance desiccation tolerance include utilizing improved vitrification medium containing trehalose, glycerol and sucrose. While improved methods for loading cells with protective agents are helpful, there is a further need to develop techniques to minimize cellular injury during desiccation. Injury and degradation may result from the high sensitivity of cells in general to prolonged exposure to osmotic stress during dry processing. Osmotic stress can cause cell death at relatively high moisture content even in the presence of protective sugars like trehalose.

The most common approach to desiccating cells involves drying in sessile droplets with suspended cells. However, desiccation using evaporative drying of sessile droplets is inherently slow and non-uniform in nature. A glassy skin forms at the liquid/vapor interface of the sample when the cells are desiccated in glass forming solutions. This glassy skin slows and ultimately prevents further desiccation of the sample beyond a certain level of dryness and induces significant spatial non-uniformity of the water content across the sample. As a result, cells trapped in the partially desiccated sample underneath the glassy skin may not vitrify but degrade due to high molecular mobility.

U.S. Pat. No. 7,883,664, in which N. Chakraborty is a common inventor, discloses a method for enhancing desiccation rate by employing microwave drying. Further, U.S. Pat. No. 8,349,252, in which N. Chakraborty is a common inventor, discloses a vitrified composition comprising trehalose for vitrification by microwave drying. However, the method cannot achieve continuous drying as the biological material's temperature increases continuously to unsafe levels and requires a complicated process control. Chakraborty et al. have also employed spin drying technique to create ultra-thin films and successfully vitrified hamster ovary cells in trehalose medium. However, this approach still suffers from the limitations that the desiccation cannot be uniformly performed across the entire sample surface. Further, the film has to be ultra-thin to vitrify successfully.

The development of a fast and practical desiccation technique to achieve very low and uniform final moisture levels across the sample might overcome the shortcomings of the anhydrous vitrification techniques. Dry preservation suffers from a major limitation in long-term storage due to the degradation of the biological material by cumulative chemical stresses encountered as the vitrification solution gets concentrated in the extra-cellular space. This results in irreversible cell damage before the cells and the vitrification solution can reach a suitably low moisture content to become glassy. Therefore, there exists a need for improved vitrification medium to vitrify biological materials by fast drying while maintaining the material's viability. A fast desiccation method with improved cell viability will tremendously facilitate long term storage of biological materials at non-cryogenic temperatures as well as overcome the challenges associated with cryogenic vitrification and storage technologies.

SUMMARY

The following summary is provided to facilitate an understanding of some of the innovative features unique to the present invention and is not intended to be a full description. A full appreciation of the various aspects of the invention can be gained by taking the entire specification, claims, drawings, and abstract as a whole.

Embodiments of the present invention solve one or more problems of the prior art by providing in at least one embodiment, a method for fast and uniform moisture removal during non-cryogenic vitrification of biological materials, In another embodiment, a preferred vitrification composition to preserve the structural integrity (physiological and/or molecular) of the biological material during fast drying is provided. The said vitrification composition comprises trehalose, glycerol and ionic buffer containing one or more large organic ions such as choline and betine, In yet another embodiment, a non-cryogenic vitrification device is provided. The vitrification device comprises providing a receptacle with walls containing a plurality of capillary channels and a requisite quantity of said biological materials and vitrification medium operably in contact with the first openings of the capillary channels, and providing an enclosure operably in communication with the second openings of the capillary channels as well as with an external environment wherein the pressure, temperature and humidity within the enclosure can be controlled, In yet another further embodiment, a vitrification and long term storage protocol for the said vitrified biological materials is provided. The protocol includes placing a requisite quantity of said biological materials with vitrification medium in a receptacle comprising a plurality of said capillary channels, employing the vitrification method of the present disclosure, packaging the said receptacle with vitrified biological materials in a protective enclosure and storing the said package between −196° C. to 60° C. temperatures for long term storage.

BRIEF DESCRIPTION OF THE DRAWINGS

The drawings are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. Exemplary aspects will become more fully understood from the detailed description and the accompanying drawings, wherein.

DETAILED DESCRIPTION

Figure 1:
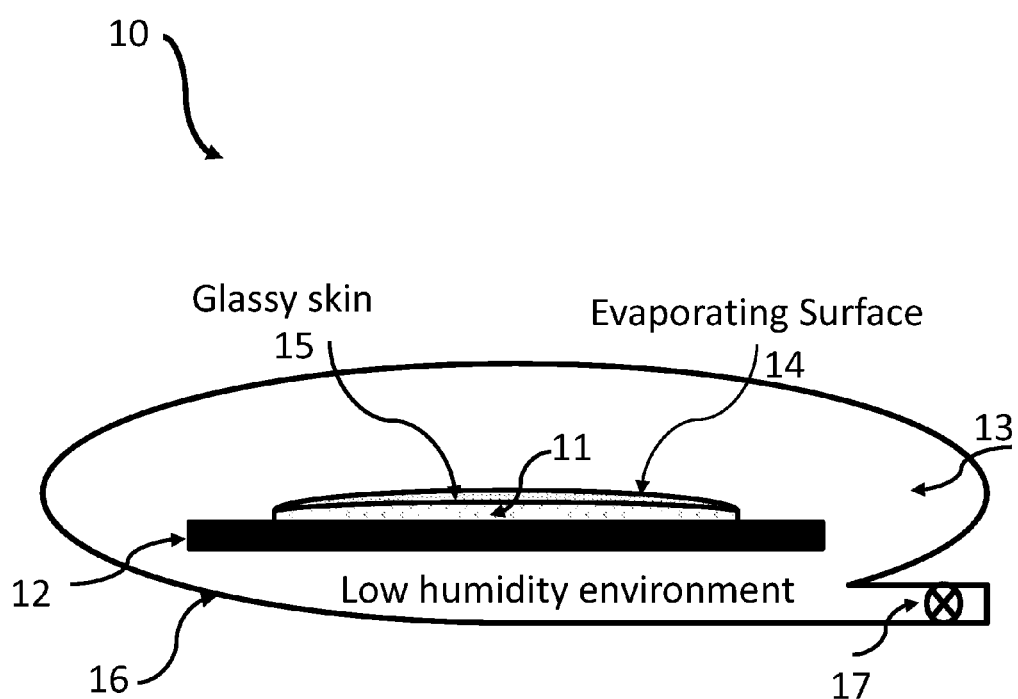
FIG. 1 is an exemplary schematic of a sessile drop vitrification by desiccation on an impervious substrate according to at least one known art.

As required, detailed aspects of the present invention are disclosed herein; however, it is to be understood that the disclosed aspects are merely exemplary of the invention that may be embodied in various and alternative forms.

Reference will now be made in detail to exemplary compositions, aspects and methods of the present invention, which constitute the best modes of practicing the invention presently known to the inventors. The Figures are not necessarily to scale. However, it is to be understood that the disclosed aspects are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific aspects and methods described herein, as specific components and/or conditions may, of course, vary. Furthermore, the terminology used herein is used only for the purpose of describing particular aspects of the present invention and is not intended to be limiting in any way.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Throughout this application, where publications are referenced, the disclosures of these publications in their entireties are hereby incorporated by reference into this application to more fully describe the state of the art to which this invention pertains.

The following terms or phrases used herein have the exemplary meanings listed below in connection with at least one aspect:

"Amorphous" or "glass" refers to a non-crystalline material in which there is no long-range order of the positions of the atoms referring to an order parameter of 0.3 or less. Solidification of a vitreous solid occurs at the glass transition temperature $T_g$. In some aspects, the vitrification medium may be an amorphous material. In other aspects, the biological material may be amorphous material.

"Glass transition temperature" means the temperature above which material behaves like liquid and below which material behaves in a manner similar to that of a solid phase and enters into amorphous/glassy state. This is not a fixed point in temperature, but is instead variable dependent on the timescale of the measurement used. In some aspects, glassy state may refer to the state the biological composition enters upon dropping below its glass transition temperature. In other aspects, the glassy state may refer to the state the vitrification mixture and/or vitrification agent enters upon dropping below its glass transition temperature. In yet other aspects, the glassy state may have the mechanical rigidity of a crystal, but the random disordered arrangement of molecules characterizes a liquid.

"Crystal" means a three-dimensional atomic, ionic, or molecular structure consisting of one specific orderly geometrical array, periodically repeated and termed lattice or unit cell.

"Crystalline" means that form of a substance that is comprised of constituents arranged in an ordered structure at the atomic level, as opposed to glassy or amorphous. Solidification of a crystalline solid occurs at the crystallization temperature $T_c$.

"Vitrification", as used herein, is a process of converting a material into an amorphous material. The amorphous solid may be free of any crystalline structure.

"Vitrification mixture" as used herein, means a heterogeneous mixture of biological materials and a vitrification medium containing vitrification agents and optionally other materials.

"Biological material", as used herein, refers to materials that may be isolated or derived from living organisms. Examples of biological materials include, but are not limited to, proteins, cells, tissues, organs, cell-based constructs, or combinations thereof. In some aspects, biological material may refer to mammalian cells. In other aspects, biological material may refer to human mesenchymal stem cells, murine fibroblast cells, blood platelets, bacteria, viruses, mammalian cell membranes, liposomes, enzymes, or combinations thereof. In other aspects, biological material may refer to reproductive cells including sperm cells, spermatocytes, oocytes, ovum, embryos, germinal vesicles, or combinations thereof. In other aspects, biological material may refer to whole blood, red blood cells, white blood cells, platelets, viruses, bacteria, algae, fungi, or combinations thereof.

"Vitrification agent", as used herein, is a material that forms an amorphous structure, or that suppress the formation of crystals in other material(s), as the mixture of the vitrification agent and other material(s) cools or desiccates. The vitrification agent(s) may also provide osmotic protection or otherwise enable cell survival during dehydration. In some aspects, the vitrification agent(s) may be any water soluble solution that yields a suitable amorphous structure for storage of biological materials. In other aspects, the vitrification agent may be imbibed within a cell, tissue, or organ.

"Storable or storage," as used herein, refers to a biological material's ability to be preserved and remain viable for use at a later time.

"Above cryogenic temperature," as used herein, refers to a temperature above −80° C. Room temperature, as used herein, refers to a temperature range between 18 and 37° C.

"Hydrophilic," as used herein, means attracting or associating preferentially with water molecules. Hydrophilic materials with a special affinity for water, maximize contact with water and have smaller contact angles with water.

"Hydrophobic," as used herein, means lacking affinity for water. Materials that are hydrophobic naturally repel water, causing droplets to form, and have small contact angles with water.

"Capillary" as used herein, pertains to or occurring in or as if in a tube of fine bore having a cross sectional area of 2000 µm$^2$ or less.

Vitrified materials are often prepared by rapidly cooling a liquid material, or small volumes of biological materials directly immersed into liquid nitrogen. The cooling reduces the mobility of the material's molecules before they can pack into a more thermodynamically favorable crystalline state. Additives that interfere with the primary constituent's ability to crystallize may produce amorphous/vitrified material. In the presence of appropriate glass forming agents it is possible to store biological materials in a vitrified matrix above cryogenic temperatures and the vitrification can be achieved by dehydration.

Some animals and numerous plants are capable of surviving complete dehydration. This ability to survive in a dry state (anhydrobiosis) depends on several complex intracellular physiochemical and genetic mechanisms. Among these mechanisms is the intracellular accumulation of sugars (e.g., saccharides, disaccharides, oligosaccharides) that act as a protectant during desiccation, Trehalose is one example of a disaccharide naturally produced in desiccation tolerant organisms.

Sugars like trehalose may offer protection to desiccation tolerant organisms in several different ways. A trehalose molecule may effectively replace a hydrogen-bounded water molecule from the surface of a folded protein without changing its conformational geometry and folding due to the unique placement of the hydroxyl groups on a trehalose molecule. A sugar molecule may also prevent cytoplasmic leakage during rehydration by binding with the phospholipid heads of the lipid bilayer. Furthermore, many sugars have a high glass transition temperature, allowing them to form an above cryogenic temperature or a room temperature glass at low water content. The highly viscous 'glassy' state reduces the molecular mobility, which in turn prevents degradative biochemical reactions that lead to deterioration of cell function and death.

Vitrification of biological materials by dehydration in the presence of glass forming sugar trehalose has been disclosed N Chakraborty, et al., *Biopreservation and Biobanking*, 2010, 8 (2), 107-114. With reference to FIG. 1, the system 10 is the most common approach to dehydrating a biological material. A sessile droplet 11 is placed on a substrate 12 and evaporatively desiccated in an enclosure 16 having low humidity environment 13. The humidity, pressure and temperature inside the enclosure can be operably controlled by a control device 17. However, desiccation using evaporative drying of sessile droplets of the system 10 is inherently slow and non-uniform in nature. A glassy skin 15 forms at the liquid/vapor interface 14 of the sample when the biological materials are desiccated in glass forming medium. This glassy skin 15 slows and ultimately prevents further desiccation of the sample beyond a certain level of dryness and induces significant spatial non-uniformity of the water content across the sample. As a result, cells trapped in the partially desiccated sample underneath the glassy skin may not vitrify but degrade due to high molecular mobility.

U.S. Pat. Nos. 7,883,664 and 8,349,252, in which N. Chakraboty is a common inventor, disclosed methods for enhancing desiccation rate by employing microwave heating. However, the method cannot achieve continuous drying as the biological material's temperature increases continuously to unsafe levels and requires a complicated process control. Chakraborty et al. have also employed spin drying technique to create ultra-thin films and enhance the desiccation rate. However, this approach still suffers from the limitations of the system 10, of FIG. 1, and the desiccation cannot be uniformly performed across the entire sample surface.

In view of the above-described limitations, one aspect of the present invention relates to a method for fast and uniform desiccation of a vitrification mixture. An object of another aspect of the present invention is to provide a device to perform the method efficiently. Another aspect of the present invention provides a protocol for storing the vitrified material.

Figure 2:
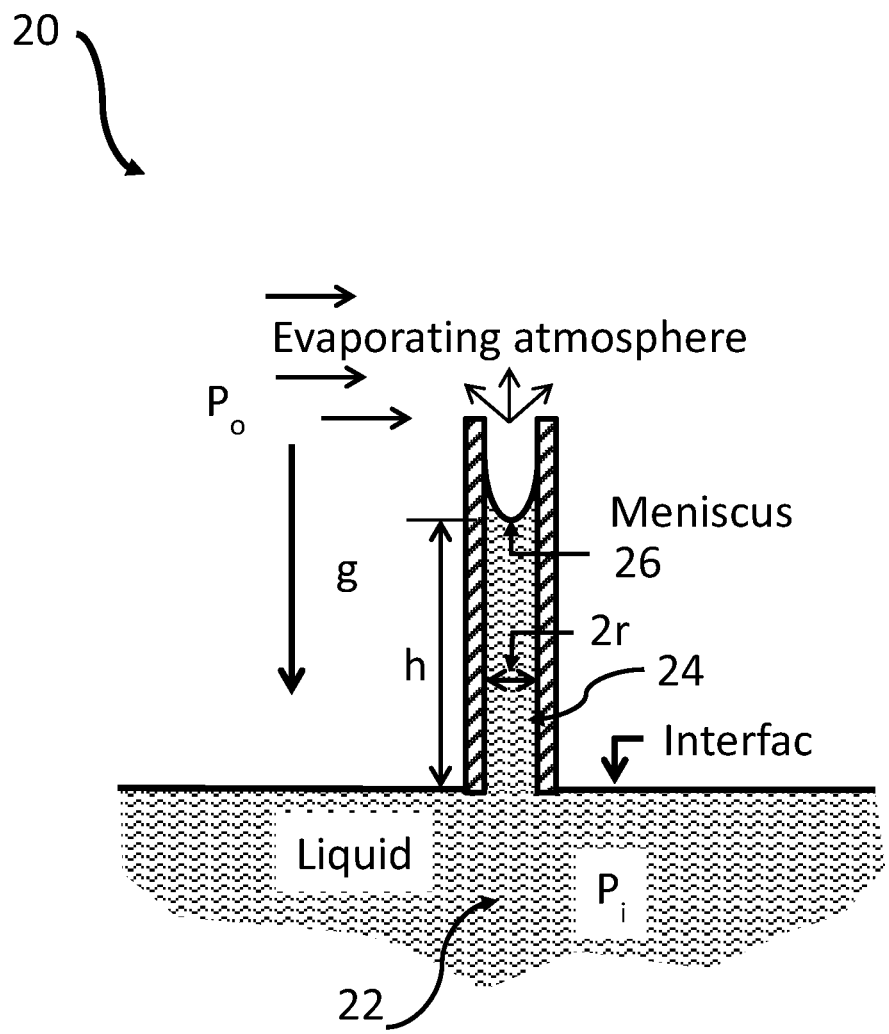
FIG. 2 is an exemplary schematic describing the mechanism of capillary assisted drying wherein the capillary force is acting opposite to gravity and the second opening is operably in communication with the desiccating environment according to at least one embodiment of the current disclosure.

With reference to FIG. 2, when a capillary 24 of uniform linear cross sectional dimension (2r, where r is ½ the cross sectional dimension) is placed in a liquid medium or heterogeneous mixture containing liquid (e.g. porous medium) 22, the liquid level will rise in the capillary to a height h which is given by;

$$h = \left(\frac{2\sigma}{\rho g r}\right)\cos\alpha; \qquad \text{(Eqn. 1)}$$

where, ρ is the density of the liquid, σ is the surface tension, α is the angle of contact, g is gravity, and the pressure at evaporating surface $P_o$=pressure in the liquid $P_i$. A negative pressure, known as a suction potential, will exist in the liquid inside the capillary. Immediately below the meniscus 26, the suction potential will be equivalent to liquid column height h. This is the height at which gravitational head balances the maximum capillary driving force causing cessation of flow, and could also be viewed as characteristic length for a given capillary. As the liquid evaporates, capillary meniscus 26 will drop resulting in capillary pressure drop or head h drop. Liquid will flow into the capillary to make up for the head loss. The drying rate $e_0$ from one (or more) capillaries with total cross-sectional area A is dependent on the flux density q flowing through the capillary can be expressed as;

$$e_0 A = q\pi r^2 \qquad \text{(Eqn. 2).}$$

If the flux density q cannot keep up with the drying rate, the air enters deeper and deeper into the capillary, and reduces the capillary pressure as well as the drying rate. Further, at high evaporation rates through fine capillaries, liquid flow may involve significant viscous dissipation with head loss which is proportional to flow velocity.

Thus, capillary assisted evaporation rate is affected by both atmospheric demand (humidity, temperature and velocity of air/gas at the evaporating surface), and (i) the characteristics of the capillary channels that generate the driving capillary force, (ii) the liquid meniscus depth, and (iii) the viscous resistance to flow through the capillary. Consequently, complex and highly dynamic interactions between capillary properties, transport processes, and boundary conditions result in wide range of evaporation behaviors. For fast drying the key parameters are: (1) the conditions that support formation and sustain a liquid network at the evaporating surface and (2) the characteristics that promote formation of capillary pressure that induce sufficient flow to supply water at the evaporating surface. In aspect 20 of FIG. 2, the capillary pressure gradient towards the surface is opposed by gravitational forces and viscous dissipation, whereas capillary pressure gradient is supported by smaller capillary diameter as well as smaller contact angle or hydrophilic capillary material. It is to be noted that smaller the capillary diameter, higher is the viscous dissipation. To achieve optimum evaporation rate, the contact angle or wettability, the length and the diameter of the capillary channel must be carefully balanced.

Figure 3:
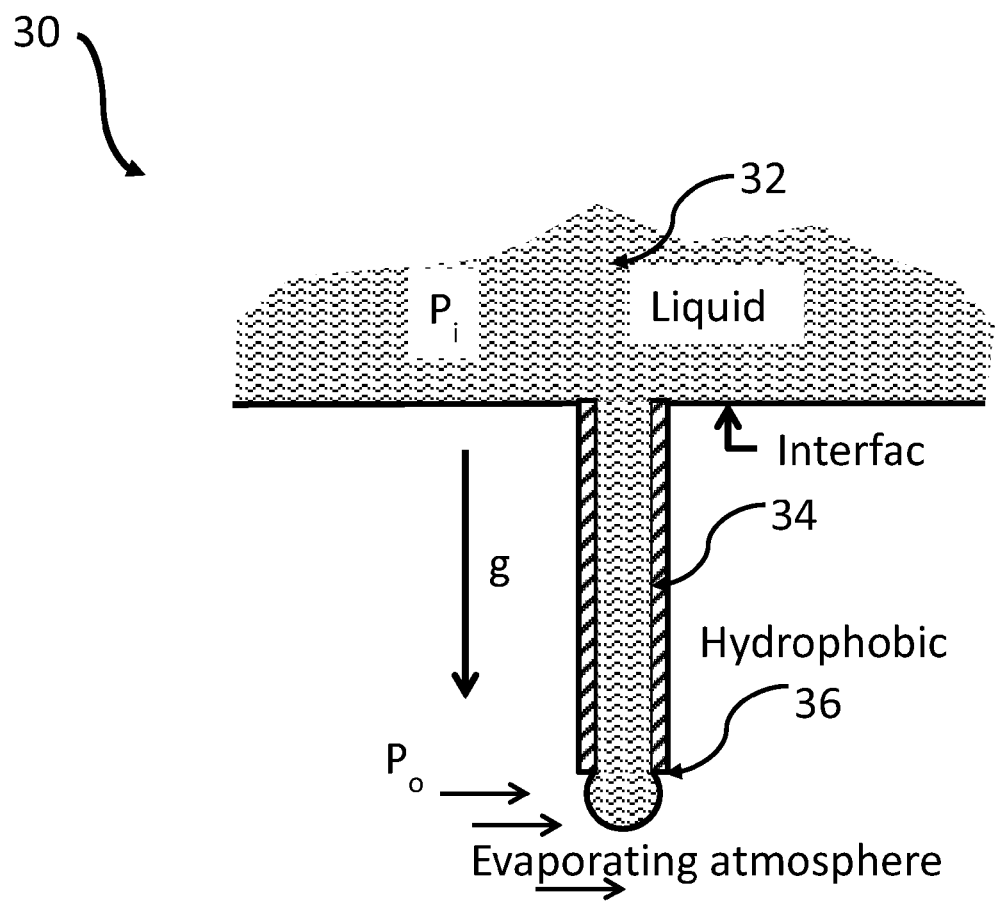
FIG. 3 is an exemplary schematic describing the mechanism of capillary assisted drying wherein the capillary force is acting in the same direction of gravity and the second opening of the capillary channel is hydrophobic and is operably in communication with the desiccating environment according to at least one embodiment of the current disclosure.
Figure 4:
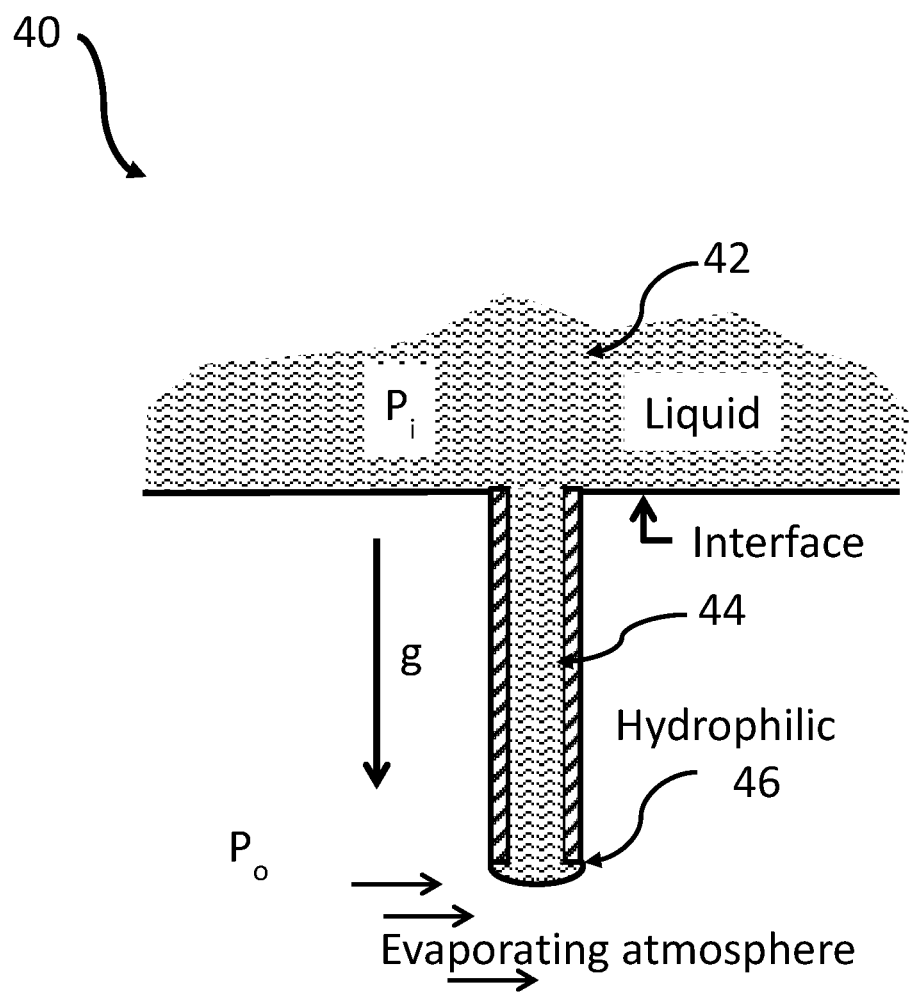
FIG. 4 is an exemplary schematic describing the mechanism of capillary assisted drying wherein the capillary force is acting in the same direction of gravity and the second opening of the capillary channel is hydrophilic and is operably in communication with the desiccating environment.

Referring to FIG. 3, aspect 30, provides a capillary drying method where the drying is performed on a support including capillary channels 34. Thus, the gravitational force instead of opposing the capillary pressure gradient, becomes additive. As a result, the capillary diameter can be enlarged, reducing the viscous dissipation which controls the evaporation rate. Further, the liquid/vapor meniscus always remains outside the capillary preventing air entry into the capillary, thus enabling steady drying till complete desiccation. As mentioned earlier, a smaller contact angle or hydrophilic capillary material favors higher capillary head and is preferred. However, an entirely hydrophilic capillary material is not preferred for best drying. Referring to FIG. 4, in aspect 40 a hydrophilic capillary material would promote the spreading of the water on the tip 46 and would form a moisture boundary layer reducing the evaporation rate. In contrast, a hydrophilic capillary 34 with a hydrophobic tip 36 of aspect 30 in FIG. 3, provides improved characteristics for drying. However, significant drying still can be achieved in the absence this combination and doesn't limit the scope of the present disclosure.

Referring to Equation 1, the capillary height was estimated based on the assumption that the pressures on the both sides of the interface are equal, i.e. $P_o = P_i$. However, a reduced pressure at the evaporating interface i.e., $P_o < P_i$, can further assist the capillary force and improve the drying rate as well as drying level. This is particularly important towards the end of the process when the moisture level is low and capillary force alone cannot sustain a liquid network at the evaporating surface.

Figure 5:
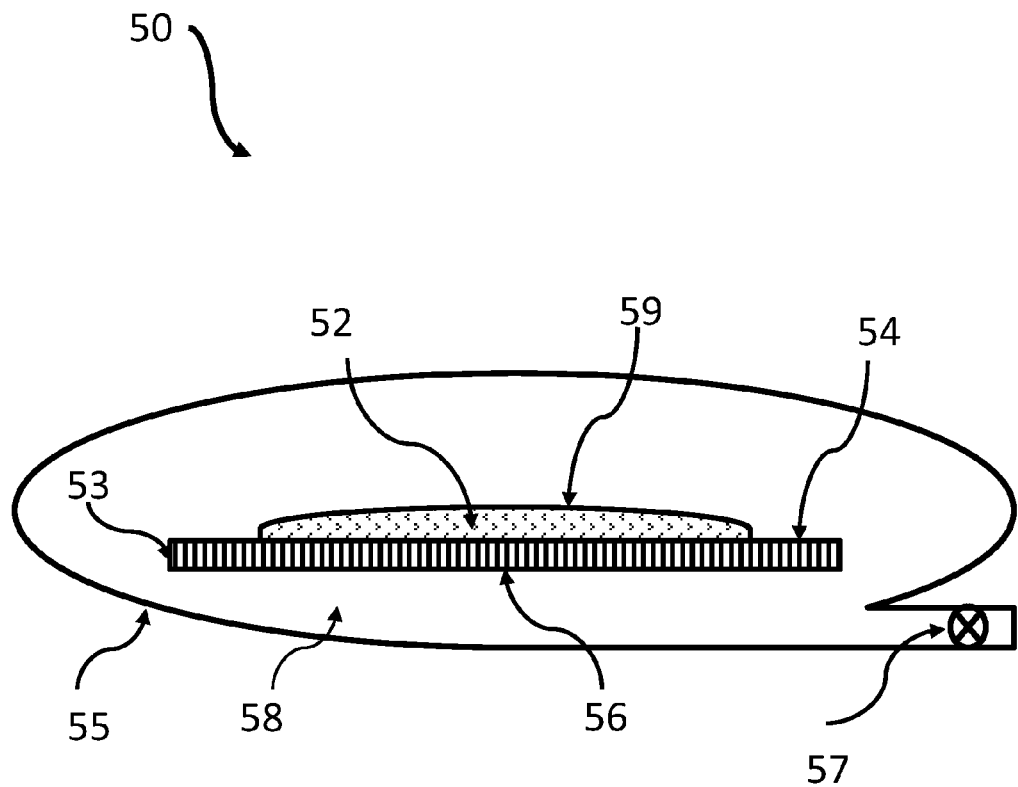
FIG. 5 shows an exemplary embodiment of capillary assisted vitrification of a sessile drop supported by a substrate comprising a plurality of capillary channels according to the teachings of the current disclosure.

Referring to FIG. 5, illustrating favorable conditions for capillary assisted drying, aspect 50 discloses a method for vitrification of biological materials, the method comprising: providing a plurality of capillary channels forming a capillary plate/membrane 53, the capillary channels having a first opening 54 and a second opening 56; placing a vitrification mixture 52 on the first opening 54, further exposing the second openings 56 and the vitrification mixture's surface 59 to a surrounding atmosphere 58 having lower humidity than the vitrification mixture; and desiccating away the said vitrification mixture by capillary action until the said vitrification mixture enters into a glassy state. The chemistry, humidity, pressure and temperature inside the enclosure 55 is controlled through a control mechanism 57.

The control mechanism 57 is simplified for illustration purposes only and can have multiple systems and mechanisms to attain the most favorable conditions for desiccation and vitrification. In some aspects, a second capillary plate/membrane similar to 53 is placed directly on top of the vitrification mixture 52 to benefit from the capillary assisted drying method of the present disclosure at the top surface of vitrification mixture 52. However, gravity will not favor the capillary force on the top. In some aspects, a flow of low humidity gas (less than 30% relative humidity) is provided across the second openings 56 of the capillary plate/membrane so as to enhance the capillary effect. Inert or relatively inert gases such as nitrogen, argon, xenon, or others may be used as a low humidity gas. In some aspects, a reduced pressure or vacuum is maintained inside the enclosure 55. In some aspects, a suction force/pressure is provided across the second opening 56 to achieve increased desiccation speed. It is to be noted that, maintaining a low humidity surrounding (optionally 5% relative humidity or less) is essential to prevent rehydration after desiccation has been performed.

Figure 6A:
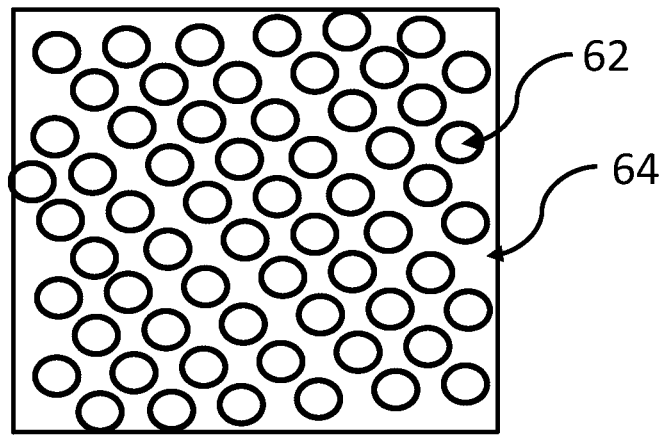
FIG. 6A shows an exemplary embodiment of a substrate comprising a plurality of capillary channels formed by making holes into the substrate.
Figure 6B:
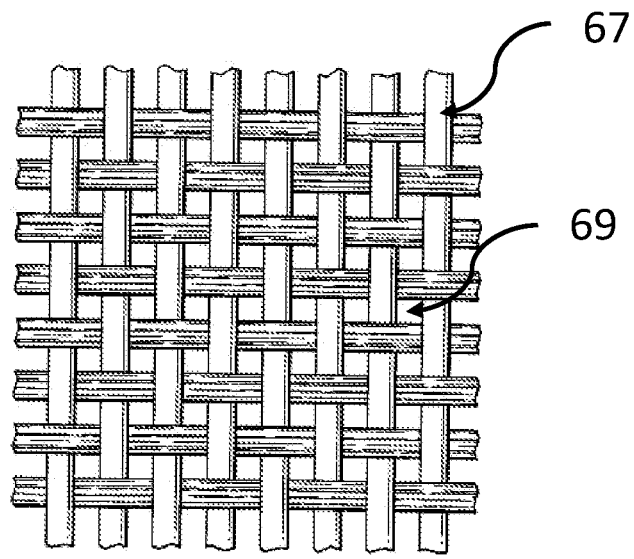
FIG. 6B shows an exemplary embodiment of a substrate comprising a plurality of capillary channels formed by weaving.

Referring to FIG. 6A, in aspect 60, the capillary plate/membrane includes a substrate 62 with cylindrical holes 64 forming a plurality of capillary channels. It must be noted that straight, substantially parallel, channels are shown for purposes of illustration only, the channels actually used may be of any cross-sectional shape and configuration suited to the purpose, illustratively oval, circular, polygonal, irregular, or other shape. For illustration purposes, FIG. 6B shows an aspect 65 where square cross section channels 69 are formed by weaving threads 67. The capillary drying plate/membrane is sufficiently thin and strong so as to provide low viscous dissipation yet to contain the biological materials during desiccation process.

A capillary channel has a length optionally defined by the thickness of a substrate that forms the channels or by one or a plurality of individual channels themselves. A capillary channel length is optionally one millimeter or less, but isn't limited to this specification. Optionally, a capillary channel length is between 0.1 microns to 1000 microns, or any value or range therebetween. Optionally, a capillary channel length is 5-100 microns, optionally 1-200 microns, optionally 1-100 microns. A capillary channel length is optionally 5, 10, 15, 20, 25, 30, 35, 40, 45, 50, 55, 60, 65, 70, 75, 80, 85, 90, 95, or 100 microns. In some aspects, the length of the capillary channels varies throughout a plurality of capillary channels, optionally in a non-uniform variation.

The cross-sectional area of the capillary channel(s) will be 2000 $\mu m^2$ or less. Optionally a cross-sectional area is from 0.01 $\mu m^2$ to 2000 $\mu m^2$, optionally 100 $\mu m^2$ to 2000 $\mu m^2$, or any value or range therebetween. Optionally, a cross-sectional area of the capillary channel(s) is 100, 200, 300, 400, 500, 600, 700, 800, 900, 1000, 1100, 1200, 1300, 1400, 1500, 1600, 1700, 1800, 1900, or 2000 $\mu m^2$ or less.

Optionally, the capillary channel(s) of the invention will have a linear cross sectional dimension, optionally a diameter, of 0.1-10 microns, or any value or range therebetween. For channels that are not circular in cross-section, this would correspond to a cross-sectional area of 0.01 square microns to 100 square microns.

The capillary drying plate/membrane may be made of a material that is not toxic to the biomaterials and doesn't react chemically or physically with the vitrification medium. This can be a suitable polymer, metal, ceramic, glass, or a combination thereof. Inert polymers or their composites are preferred. In some aspects, a capillary membrane is formed from polydimethylsiloxane (PDMS), polycarbonate, polyurethane, polyester (e.g. polyethylene terephthalate), among others. Illustrative examples of a capillary channel containing membrane suitable as a surface in the devices and processes provided herein include hydrophilic filtration membranes such as those sold by EMD Millipore, Bellerica, Mass. A capillary drying plate/membrane is optionally formed of a material that is non-reactive to the biological material or vitrification agent, or other reagents/materials used in the system. A non-reactive capillary drying plate/membrane will not substantially bind, alter, or otherwise produce a chemical or physical association with a component of a vitrification medium (e.g. biological sample). A capillary drying plate/membrane is optionally not derivitized. Optionally, capillary channels may be formed in a substrate of desired material and thickness by PDMS formation techniques, laser drilling, or other bore forming technique as is known in the art.

Figure 7A:
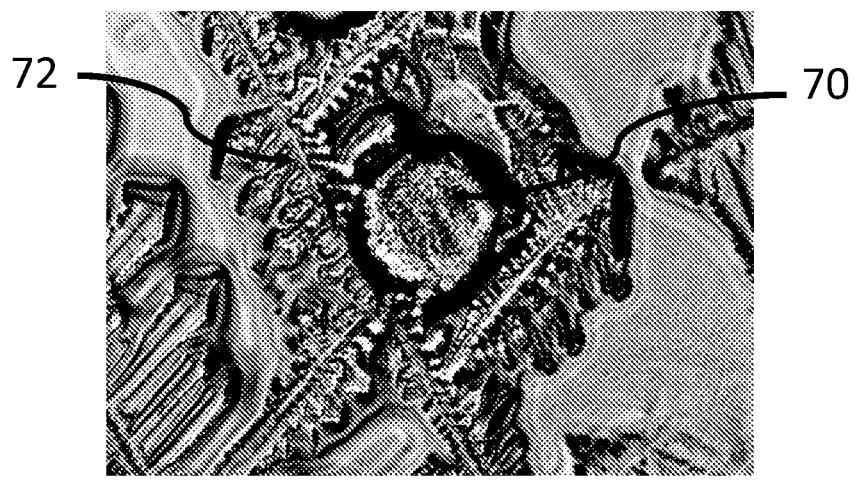
FIG. 7A shows an exemplary result of mouse oocyte desiccation performed according to the current teachings wherein the vitrification medium lacks glass forming agent trehalose.

The presence of appropriate vitrification agents in the vitrification mixture is critical as the mixture desiccates. The fast desiccation method by itself doesn't guarantee the viability of the cells or other vitrified biological material. A vitrification material/agent that forms glass, or that suppress the formation of crystals in other materials is required. The vitrification agent(s) may also provide osmotic protection or otherwise enable cell survival during dehydration. Referring to FIG. 7A, undesirable and harmful dendritic structures 72 that signify crystallization as well as compromised/damaged oocyte 70 can be seen in the sample when it was desiccated employing the method of the current disclosure in the absence of any glass forming vitrification agent. The details of the experimental protocol is provided in the Example 2.

Illustrative examples of a vitrification agent include, but are not limited to, dimethylsulfoxide, glycerol, sugars, polyalcohols, methylamines, betines, antifreeze proteins, synthetic anti-nucleating agents, polyvinyl alcohol, cyclohexanetriols, cyclohexanediols, inorganic salts, organic salts, ionic liquids, or combinations thereof. A vitrification medium optionally contains 1, 2, 3, 4, or more vitrification agents.

The vitrification medium includes a vitrification agent at a concentration that is dependent on the identity of the vitrification agent. Optionally, the concentration of the vitrification agent is at a concentration that is below that which will be toxic to the biological sample being vitrified where toxic is such that functional or biological viability is not achieved upon subsequent sample use. The concentration of a vitrification agent is optionally 500 µM to 6 M, or any value or range therebetween. For the vitrification agent trehalose, the concentration is optionally from 1 M to 6 M. Optionally, the total concentration of all vitrification agents when combined is optionally from 1M to 6M.

The vitrification medium optionally includes water or other solvent, a buffering agent, one or more salts or other components. A buffering agent is any agent with a pKa of 6 to 8.5 at 25° C. Illustrative examples of buffering agents include HEPES, TRIS, PIPES, MOPS, among others. A buffering agent is provided at a concentration suitable to stabilize the pH of the vitrification medium to a desired level.

Figure 7B:
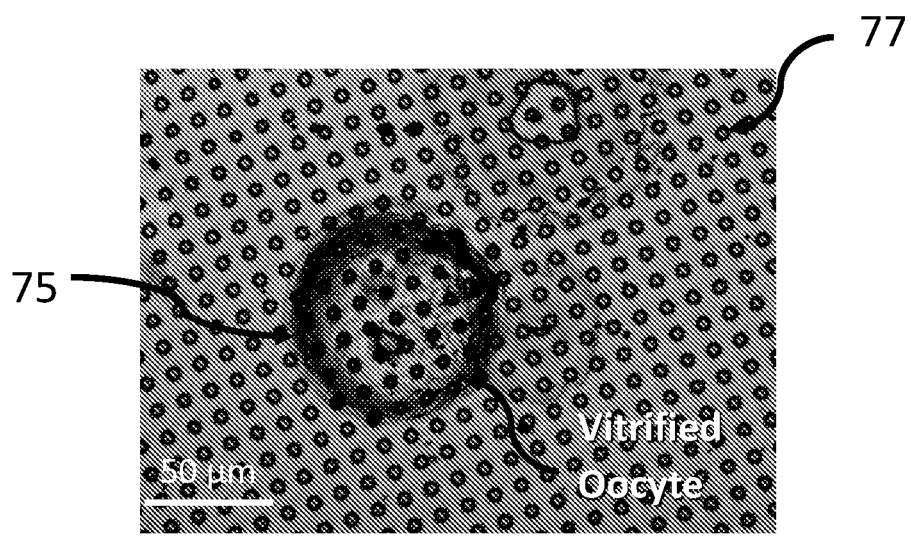
FIG. 7B shows an exemplary result of mouse oocyte desiccation performed according to the current teachings wherein the vitrification mixture contains trehalose, HEPES, choline and betine.
Figure 8A:
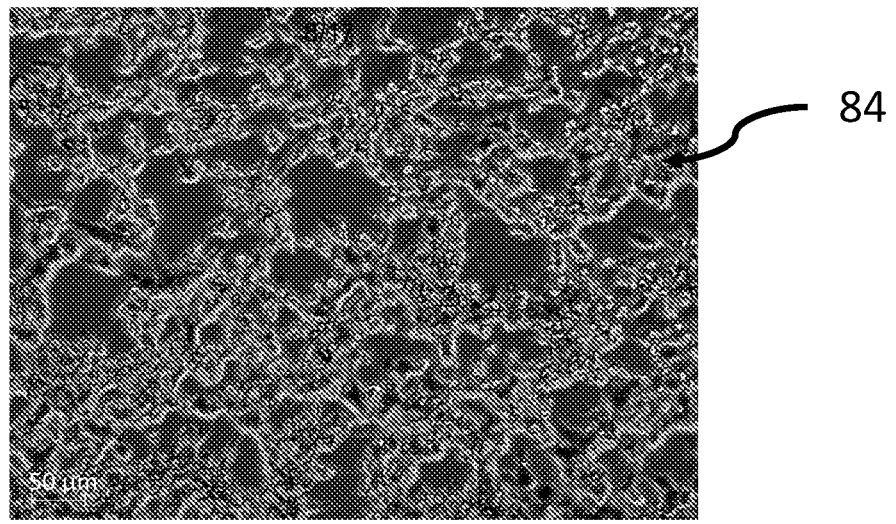
FIG. 8A illustrates the formation ice crystals during fast drying of ultra-thin films comprising Chinese Hamster Ovary Cell in the absence of vitrification agent trehalose.
Figure 8B:
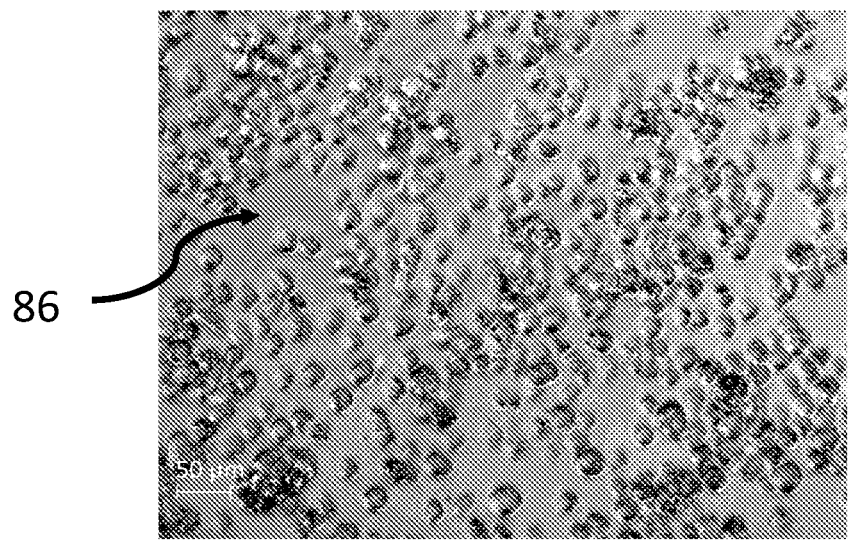
FIG. 8B shows the complete vitrification during fast drying of ultra-thin films comprising Chinese Hamster Ovary Cell and vitrification medium containing Chinese Hamster Ovary Cells, 20 mM HEPES, 120 mM ChCl, 1.8M Trehalose, 60 mM Betine and water.

Referring to FIG. 7B, complete vitrification was achieved when mouse oocytes were desiccated employing the method of the current disclosure utilizing a vitrification mixture containing trehalose (1.8 M), glycerol, choline and betine (60 mM). The integrity of the oocyte 75 is evident and signifies the benefits of the capillary 77 assisted vitrification method disclosed herein. The importance of appropriate vitrification medium is further illustrated in FIGS. 8A and 8B. Even at the fast desiccation rates possible in ultra-thin films (spin drying such as is used on prior methods as illustrated in FIG. 1) homogeneous vitrification is not guaranteed, and FIG. 8A shows formation of ice crystals 84 in the vitrification mixture comprising Chinese hamster ovary (CHO) cells but no glass forming agent. On the contrary, the a vitrification medium comprising trehalose, HEPES, ChCl, and Betine resulted in uniformly vitrified 86 biological material under ultra-thin films (spin drying) configuration as shown in FIG. 8B. Compared to spin drying, the capillary assisted desiccation method disclosed herein doesn't restrict the biological material mixture to conform to ultra-thin film form to achieve very fast desiccation rates of 3 gH$_2$O/gdw/min-2 gH$_2$O/gdw/min.

Figure 9:
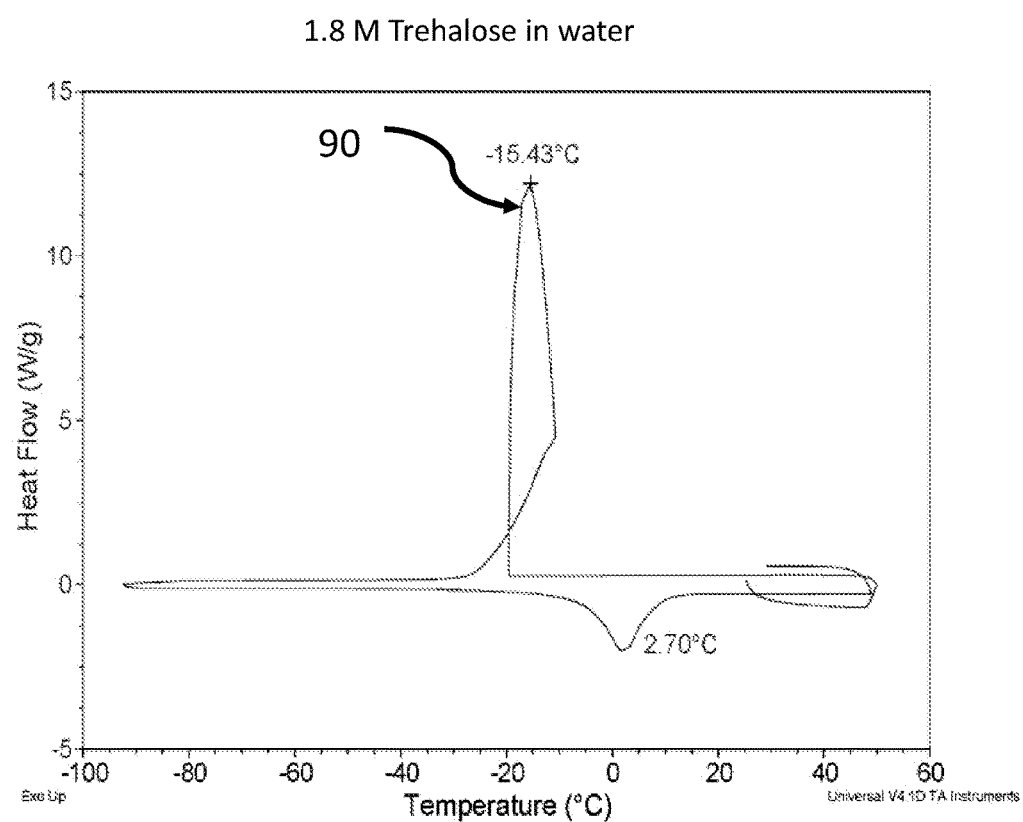
FIG. 9 shows the glass transition temperature of a vitrified medium containing Chinese Hamster Ovary Cells, 1.8 M trehalose and water.
Figure 10:
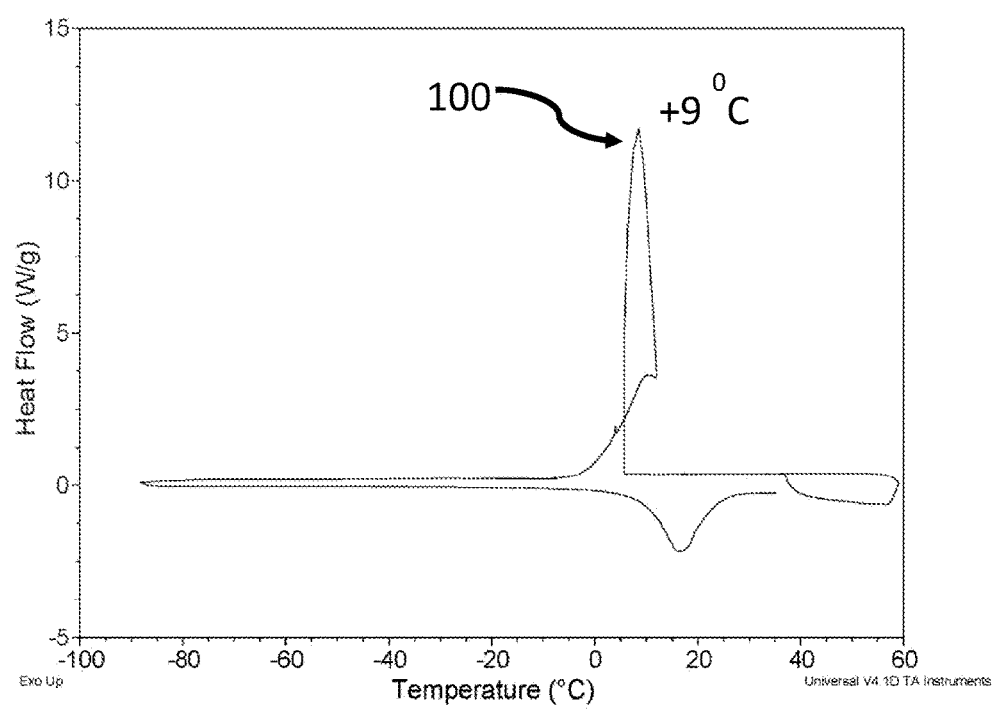
FIG. 10 shows the glass transition temperature of a vitrified medium containing Chinese Hamster Ovary Cells, 20 mM HEPES, 120 mM ChCl, 1.8M Trehalose, 60 mM Betine and water.
Figure 11:
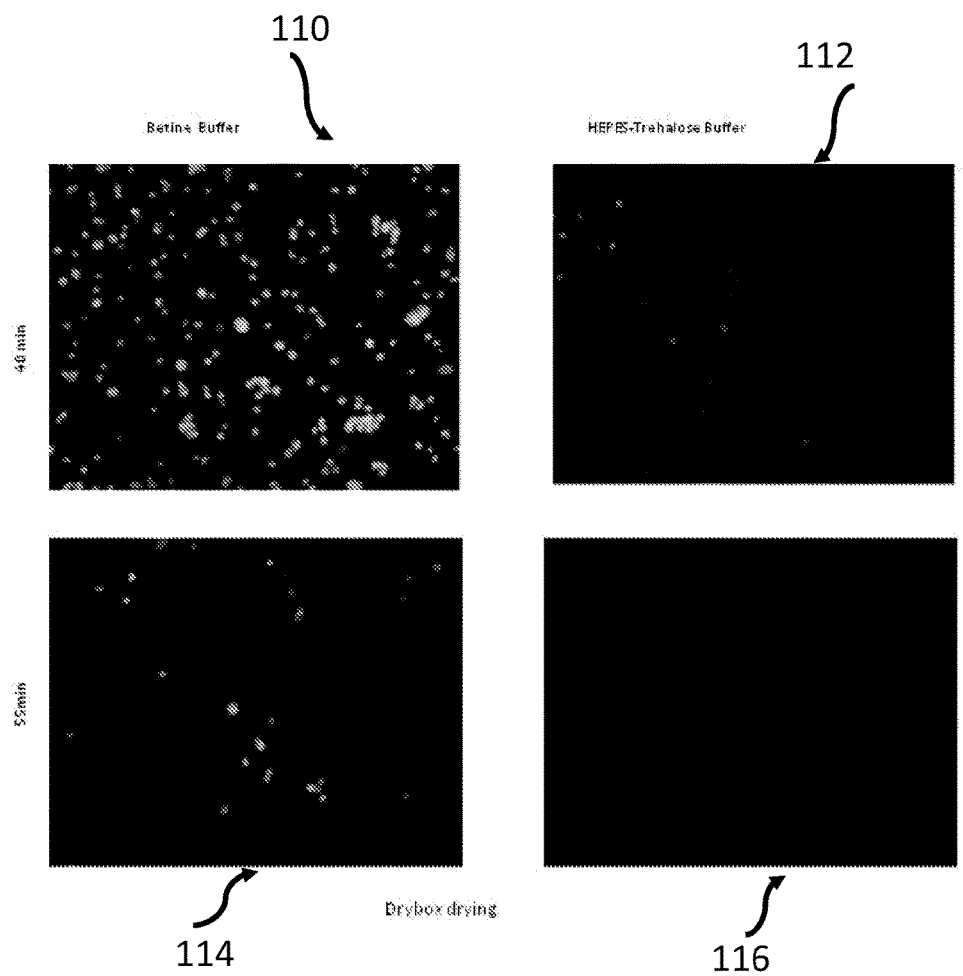
FIG. 11 demonstrates the efficacy of large organic ions Betine buffer compared to HEPES buffer on the viability of vitrified Chinese Hamster Ovary Cell desiccated in a conventional dry box where the bright spots correspond to live cells (green) and the darker gray spots correspond to dead (red) cells.

Trehalose, a glass forming sugar, has been employed in anhydrous vitrification and may provide desiccation tolerance in several ways. Referring to FIG. 9, differential scanning calorimetry shows that a vitrified 1.8M trehalose in water has a glass transition temperature 90 of −15.43° C. To achieve vitrification above water freezing point 0° C., this concentration isn't ideal and higher concentrations (6-8M) are required which could be damaging to the biological materials. Referring to FIG. 10, a vitrified mixture including 1.8M trehalose, 20 mM HYPES, 120 mM ChCl, and 60 mM Betine shows a glass transition temperature, 100 of +9° C. Further attention is drawn to the influence of the buffering agents. As shown in FIG. 11, the use of Betine buffer that contains large organic ions shows remarkable influence on the live/dead count 110 of Chinese hamster ovary (CHO) cells after 40 minutes of desiccation in a conventional dry box compared to the use of HEPES 112, which also contains large organic ions. Plates 114 and 116 further emphasize this in terms of live and dead counts after 55 minutes.

An exemplary vitrification medium for the capillary assisted vitrification method disclosed herein may include trehalose, and one or more buffering agents containing large organic ions (>120 kDa) such as choline or betine or HEPES as well as buffering agent(s) containing small ions such as K or Na or Cl. The influence of this vitrification medium composition on the cell membrane integrity under fast desiccation method of the current disclosure where ultra-low moisture levels (e.g. 0.1 gH2O/gdw or less) can be instantly achieved are further illustrated in FIGS. 15 and 16 using a vitrification medium including trehalose (to preserve/stabilization large biomolecules), glycerol (to preserve/stabilize small biomolecules and prevent molecular mobility at interstitial spaces), and choline chloride buffer. This exemplary composition doesn't limit the scope of using alternative formulations for the method disclosed herein.

The capillary assisted vitrification method may be performed at a temperature from −80° C. to +60° C. The temperature range is optionally where the mobility of water molecules in the sample is high and the temperature is not detrimental to the health and viability of the biological material. This would vary from material to material as well as the composition of the vitrification medium. In some aspects, the vitrification temperature is 0.1° C. to 40° C. Optionally, the vitrification temperature is 4° C. to 26° C. Optionally, the vitrification temperature is 25° C.

The capillary assisted vitrification method may be performed in a dry atmosphere or environment. A dry environment is an environment with a humidity level below saturation. In some aspects, the humidity level of the environment, such as the environment on the second side of the capillary tube is 30% relative humidity or less, optionally 20% or less, optionally 10% or less, optionally 5% or less.

A dry environment optionally has a humidity between 1% and 30% or any value or range therebetween, optionally between 1% and 5%.

The capillary assisted vitrification method may be performed in a low pressure environment (less than 1 atm (760 mmHg)). A low pressure environment will have favorable impact on the rate or vitrification. The environmental pressure is optionally 100 mmHg or 0.1 atm. Optionally, the environmental pressure is from 10 mmHg to 760 mmHg, or any value or range therebetween. Optionally, the environmental pressure is from 10 mmHg to 200 mmHg.

The capillary assisted vitrification method may be performed for a desiccation time. A desiccation time is a time sufficient to promote suitable drying to vitrify the vitrification medium. A desiccation time is optionally 1 second to 1 hour. Optionally, a desiccation time is 1 second to 50 min, optionally 5 seconds to 60 min. Desiccation time may vary dependent on the sample type or physical characteristics and the particulars of the capillary channels.

Figure 17:
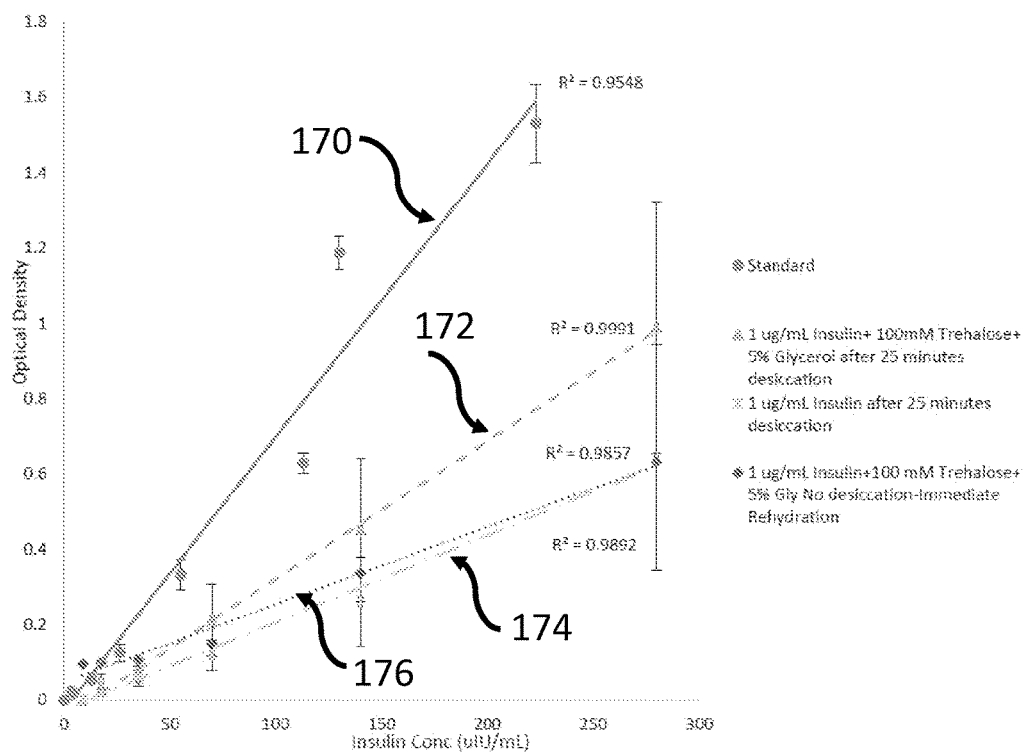
FIG. 17 shows the enhanced retention of insulin activity when desiccated according to the vitrification method as described herein where the insulin activity was measured by ELISA after rehydration of the samples where 170 illustrates the standard, 172 illustrates the results after desiccation using a sample of 1 μm insulin, 100 mM trehalose, 5% glycerol and 25 min desiccation time demonstrating excellent activity recovery, 174 illustrates 1 μm insulin after 25 min of desiccation, and 176 illustrates 1 μm insulin in 100 mM trehalose, 5% glycerol and 0 min desiccation time.

The benefits of the capillary assisted vitrification method disclosed herein are further illustrated in FIG. 17. Insulin samples when identically desiccated in the absence of vitrification agent, significant loss in activity, 174, occurs compared to that of desiccated in the presence of vitrification agent, 172. Further, the presence of vitrification agent itself is not sufficient to retain the insulin activity, 176, without desiccation. In general, significant level of insulin activity can be preserved following the capillary assisted vitrification method disclosed in this invention. Various proteinous material can be stabilized following the capillary assisted vitrification method disclosed in this invention. It is appreciate that these vitrified biological materials can be sealed in protective packages, for transportation and long term storage. Further, some of the vitirfied biological samples can be stored in ambient temperatures without requiring a cold chain. They can be utilized upon rehydration. Examples include but not limited to insulin, interleukin 1, interleukin 2, tetanus and hepatitis vaccines etc.

Figure 12:
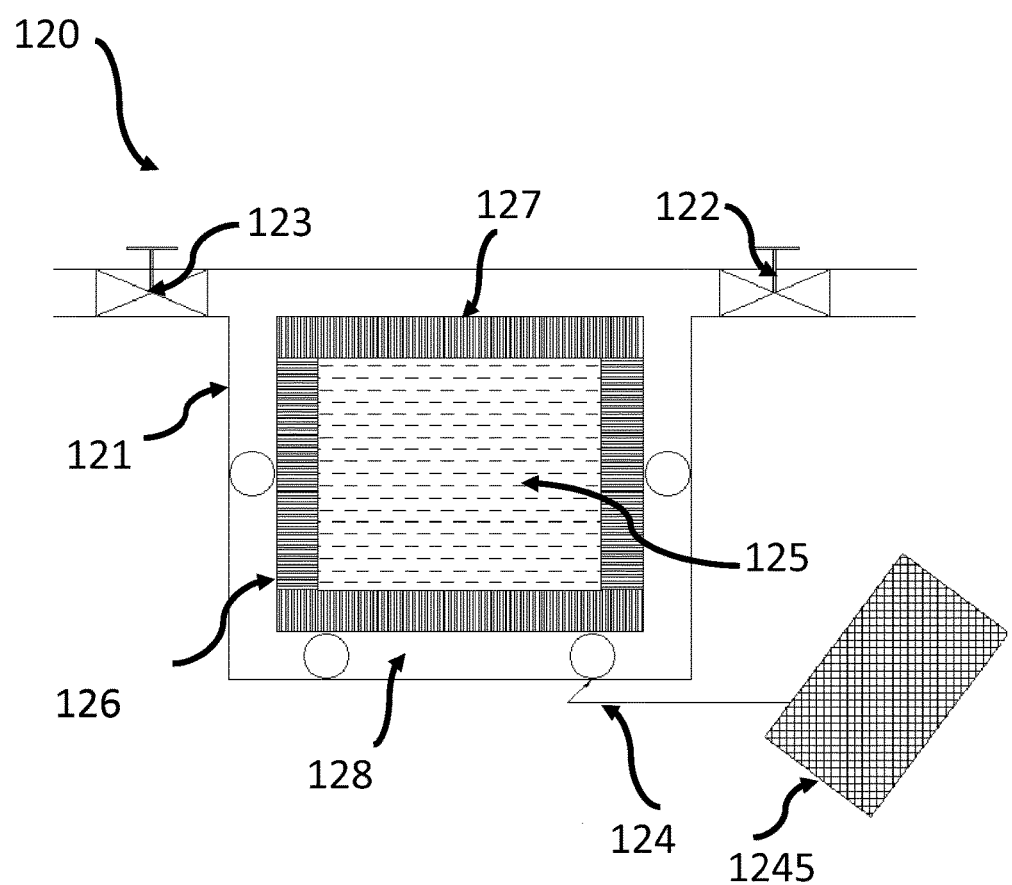
FIG. 12 shows an exemplary embodiment of a capillary assisted vitrification device according to the teachings of the current disclosure.

Referring to FIG. 12, aspect 120 illustrates an exemplary non-cryogenic biological material vitrification device to exploit the benefits of the capillary assisted vitrification method as provided herein, including: a receptacle 126 made of capillary drying plate/membrane of the current disclosure, having a first capillary opening inside the receptacle and a second capillary opening outside the receptacle; a removable lid 127 made of capillary drying plate/membrane of the current disclosure to fill a requisite quantity of said vitrification mixture 125 within the receptacle wherein said vitrification mixture is operably in contact with the first openings of the capillary channels; and an enclosure 121 operably in gaseous communication with the second openings of the capillary channels as well as with an external environment wherein the pressure, temperature and humidity within the enclosure can operably be controlled. The outside surface of the receptacle 126 maintains a gap 128 from the enclosure 121 boundary by placing perforated separators 124 to facilitate gas flow and desiccation action. An enlarged view of separator 124 is shown at 1245.

The enclosure of aspect 120 is impervious to moisture and gas and has sealable inlet(s) 122 and outlet(s) 123. The sealable inlet(s) and outlet(s) enable flow of gas across or maintain reduced pressure across the outside surface of the receptacle in order to enhance desiccation action. There may be a single or a plurality of inlets or outlets. The sealing mechanism may be mechanical or adhesive based or thermal consolidation (heat sealing). The capillary assisted vitrification method can be carried out in-situ by connecting the inlet(s) and outlet(s) to appropriate devices that can control the humidity, pressure and temperature inside the enclosure. Very fast desiccation is achieved due to enhanced capillary contact area with the vitrification mixture from all sides. This also enables vitrification of larger volumes of vitrification mixture which is a serious limitation of prior methods and systems. In general, the thickness of the sample will be 1 centimeter or less. Optionally, the thickness will be about 1 millimeter or less. It is understood that the thickness specification of aspect 120 is along the vertical axis of the picture and can be interchanged in a three dimensional construct. The method can be performed across large area.

Upon completion of the desiccation process to a desired humidity level, the inlet and outlet are sealed to prevent rehydration of the vitrified material. Alternatively the receptacle can be utilized to desiccate the vitrification mixture in a separate chamber employing the method disclosed here and then sealed in the enclosure 121. The device 120 can be configured into a wearable device optionally wherein the top lid 127 and external enclosure along the seal line 122 and 123 can be removed and adhesively attached to the application surface. Many possible configurations and applications are possible. Illustrative examples of a wearable device can be found in U.S. Patent Application Publication No: 2011/0054285 A1.

Figure 13:
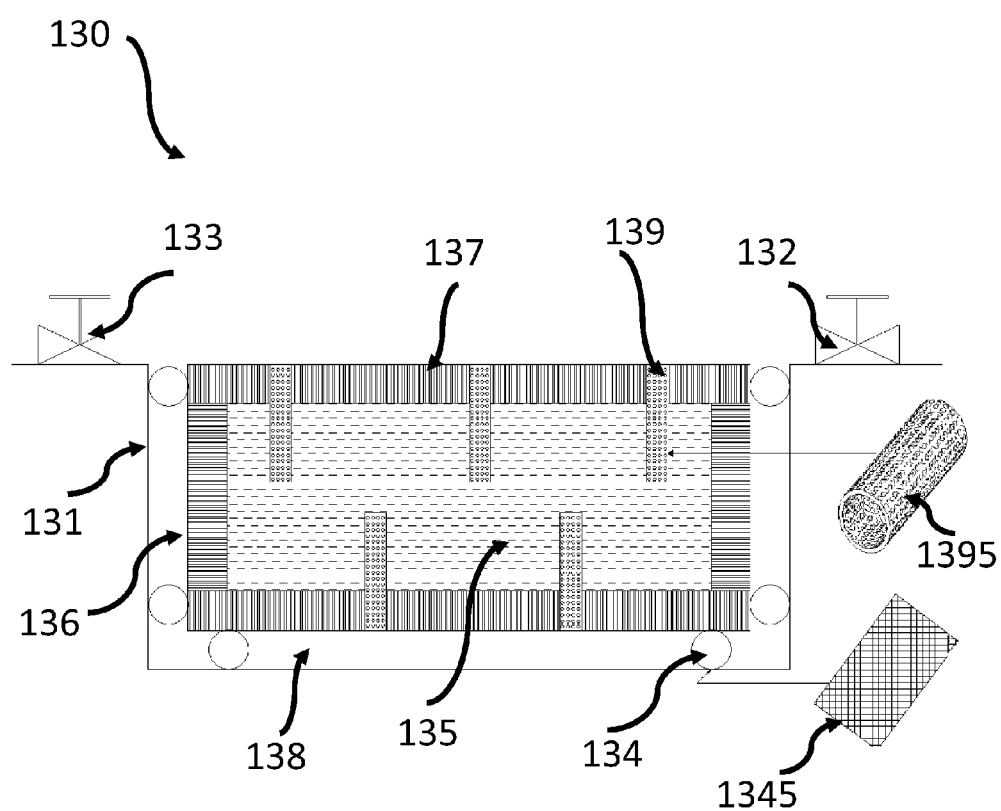
FIG. 13 shows another exemplary embodiment of a capillary assisted vitrification device according to the teachings of the current disclosure, wherein internal capillary pipes/wicks are provided within the vitrification mixture.

Referring to FIG. 13, further enhancement to the device is provided in another aspect 130, wherein plurality of capillary pipes/wicks 139 operably in communication with the vitrification mixture and the enclosure environment is provided in order to enhance desiccation action. This additional feature would enable desiccation of thicker volume of vitrification mixture. A distinction between the capillary channels of the current disclosure and capillary pipe 139 must be made. Capillary device 139 can be a hollow cylinder comprising the characteristics of the receptacle 136 as shown in 1395. As such, a pipe can be envisioned as a substantially tubular substrate of capillary channels that extends into the sample so as to effectively increase the surface area of the environment external to the sample. The end of the pipe in contact with the vitrification mixture is optionally closed. Alternatively, a wick comprising capillary channels can be also utilized, however, a pipe is preferred. Most of the discussions pertaining to aspect 120 are also applicable to aspect 130 and are repeated.

Figure 14:
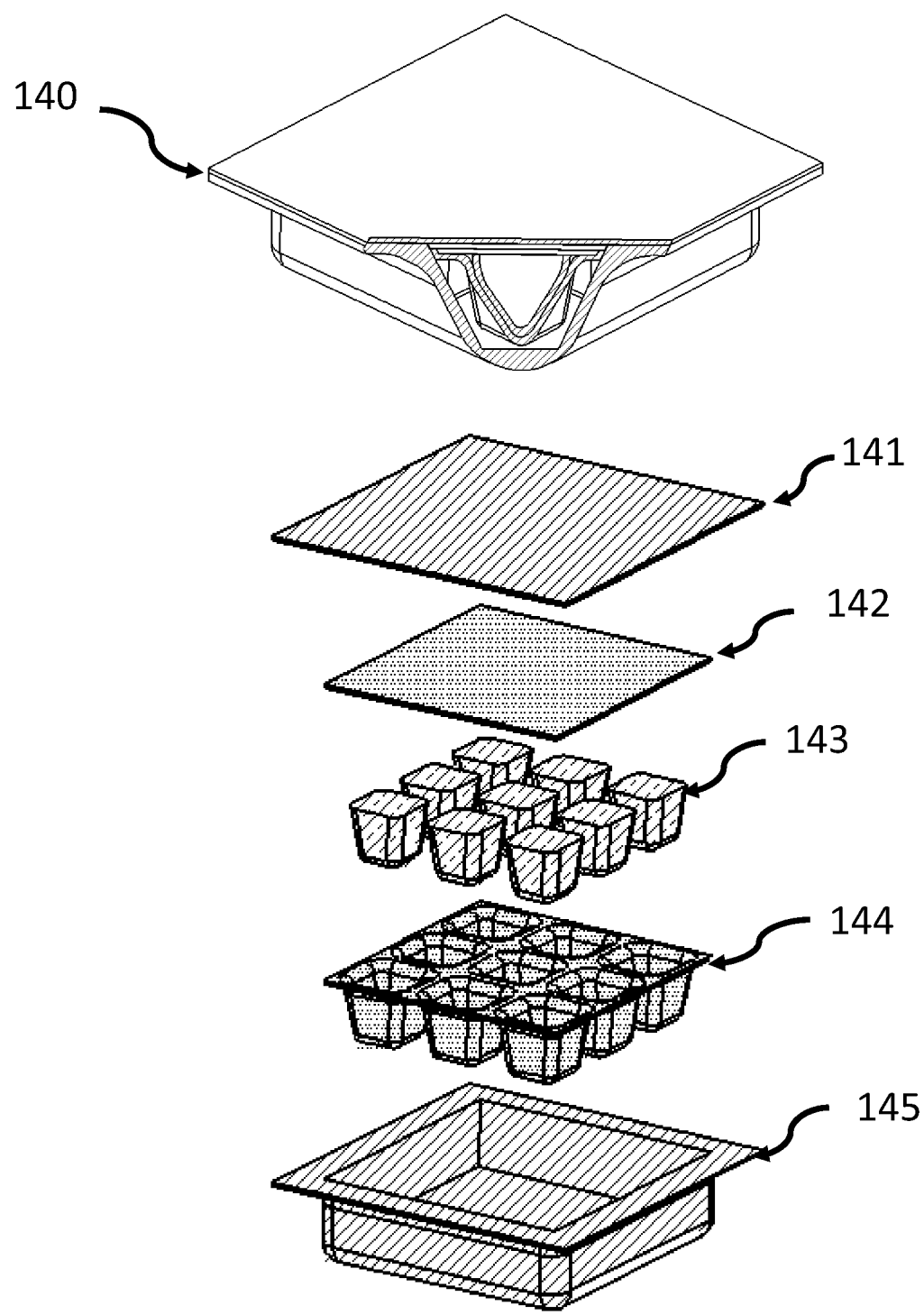
FIG. 14 shows yet another exemplary embodiment of a capillary assisted vitrification device according to the teachings of the current disclosure, wherein multiple cavities with inter cavity drying space and one common lid is provided.

Referring to FIG. 14, an additional aspect 140 is provided including a receptacle formed of multiple cavities 144 with inter cavity drying space and one common lid 142 in order to enhance desiccation action. Alternatively, each cavity can also have individual lids. Specification 141 and 145 constitute the external enclosure and 143 is the vitrification mixture including the sample. Although the inlets and outlets of the device are not shown in the picture, the device operates according to the teachings of the current disclosure and discussions pertaining to aspect 120 and 130 are applicable to this aspect. Further, the capillary pipes/wicks of aspect 130 can also be deployed in this aspect. The devices in aspects 120, 130, and 140, are sufficiently flexible and reconfigurable to become a wearable device.

The duration a biological material may remain viable in vitrified state during storage above cryogenic temperature may vary from one sample material to the next. In some aspects, a biological material may remain viable while in storage above cryogenic temperature for 2-20 days. In other aspects, a biological material may remain viable while in storage above cryogenic temperature for 10 weeks. In other aspects, a biological material may remain viable in storage above cryogenic temperature for up to one year. In other aspects, a biological material may remain viable while in storage above cryogenic temperature for up to 10 years.

Alternatively, after vitrification above cryogenic temperatures employing the teachings and devices of the current disclosure, the vitrified biological material can be stored at cryogenic temperatures for very long periods. For many biological materials, this is a preferred approach to avoid cryoinjury that commonly occurs during direct vitrification at cryogenic temperatures. A preferred approach in one aspect is to vitrify the biological materials at room temperatures utilizing low concentrations of vitrification agents (e.g. <2M trehalose) and then immediately store at cryogenic temperatures. Therefore, the said device is optionally made out of materials storable at a temperature between −196° C. to 60° C. following the vitrification according to the teachings of the current disclosure.

Figure 15:
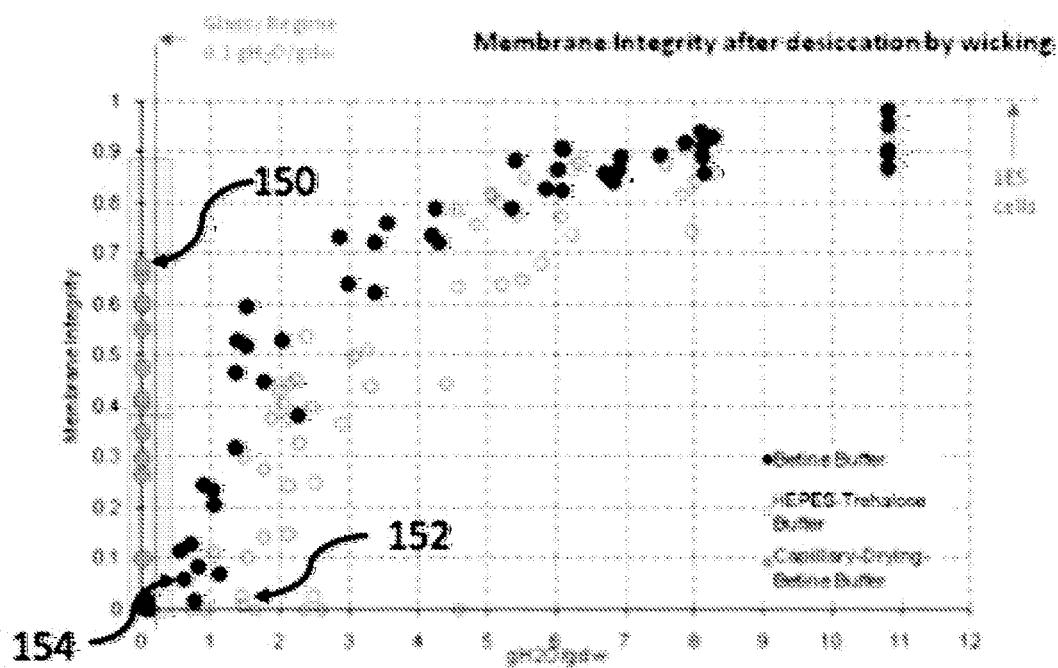
FIG. 15 shows the cell membrane integrity retention efficacy of Chinese Hamster Ovary Cells when desiccated according to the current teachings compared to conventional dry box desiccation method, where the level of dryness achieved by the end of the process is expressed in units of gH$_2$O/gdw and 150 refers to capillary-drying betine buffer, 154 refers to betine buffer, and 152 (open circles) refers to HEPES-trehalose buffer system.
Figure 16:
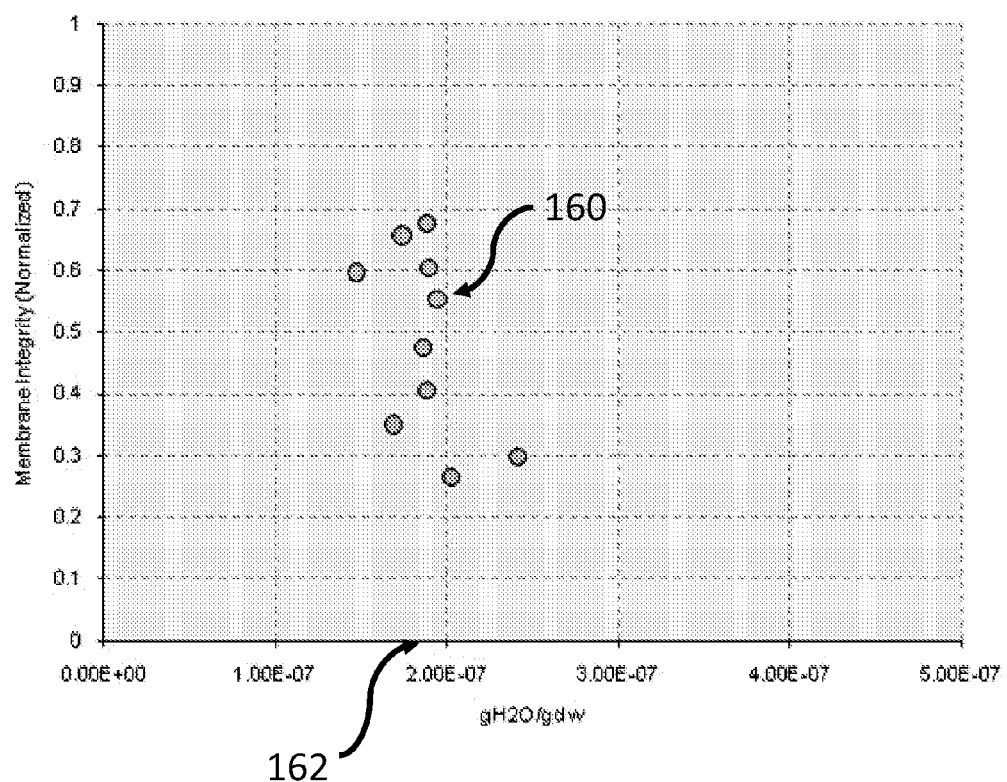
FIG. 16 shows the ability to achieve extremely low moisture level while retaining cell membrane integrity of Chinese Hamster Ovary Cells when desiccated using the methods of Example 1 illustrating the data 150 of FIG. 15 on expanded scale where the level of dryness achieved by the end of the process is expressed in units of gH$_2$O/gdw.

Further benefits of the disclosed method and devices rare illustrated in FIGS. 15 and 16. Referring to FIG. 15, the cell membrane integrity of desiccated Chinese hamster ovary (CHO) cells is compared at different moisture levels. Open circles 152 represent the membrane integrity vs moisture level while desiccating a vitrification mixture comprising 1.8M trehalose with HEPES buffer in a conventional dry box. As can be seen the cell membrane is completely destroyed by the time the moisture level reached 1 g$H_2O$/gdw. When Betine buffer was utilized in dry box desiccation process the membrane integrity represented by closed circles 154 improved compared HEPES buffer, however the membranes were almost destroyed when the moisture reached 1 g$H_2O$/gdw level. The benefits of capillary assisted fast desiccation method disclosed herein is illustrated by the closed circles 150 demonstrating that the membrane integrity is largely preserved even when the moisture level has reached extremely low level that is not feasible in conventional dry box desiccation processes. The moisture levels that are achievable by the disclosed method is further illustrated in FIG. 16. While Betine buffer helps in the preservation of the membrane integrity, the fast desiccation process of the current disclosure vitrifies the biological materials before even they realize which is largely responsible for the retention their integrity.

EXAMPLES

1. Experiments with Chinese Hamster Ovary (CHO) Cells

Cell Culture: Chinese hamster ovary (CHO) cells were obtained from American Type Culture Collection (ATCC, Manassas, Va.), and cultured in Dulbecco' modified Eagle's medium (DMEM) (Invitrogen, Carlsbad, Calif.) supplemented with 10% fetal bovine serum (Atlanta Biologicals, Norcross, Ga.) and 2% penicillin-streptomycin (10 U/mL penicillin G and 10 μg/mL streptomycin sulfate, Invitrogen, Carlsbad, Calif.). Cultures were maintained in 25-$cm^2$ T-flasks (Corning Incorporated, NY) at 37° C. and equilibrated with 10% $CO_2$-90% air. Following cell culture to desired confluency of 70%, the cells were trypsinized, pelleted and re-dispersed to create a concentration of $1 \times 10^5$ cells/mL in DMEM.

Device Assembly: A PDMS cast was created having a dimension of 0.25 inch×0.38 inch having a central circular cavity (0.05 inch) and a polypropylene membrane (obtained from Sterlitech Corporation, Kent, Wash.) having pore sizes of 5 μm and thickness of 100 μm was placed on it. These pores provided the desired capillary action to desiccate the cells. This assembly was utilized as the capillary device. The entire set-up was housed inside a custom-built enclosure (polystyrene, 6×8×6 inches) containing a low moisture atmosphere (~2% RH) and was purged with medical grade nitrogen to prevent moisture pickup through the open surface of the sample. A lid attached to a computer-controlled micro-pump (Dolomite, Charlestown, Mass.) was placed on the cavity to facilitate fast removal of moisture from the samples through the capillary channels.

Desiccation: After placing a 20 μL sample of cells suspended at a concentration of $1 \times 10^5$ cells/mL on top of the capillary substrate, the micro pump was initiated (1 mL/min) to desiccate the sample. The desiccation of the biological sample took place within 5 secs. Desiccation experiments were conducted with cell samples without glass forming agents such as trehalose as well as with a vitrification medium comprising HEPES: 20 mM, ChCl: 120 mM, Trehalose: 1.8M, Beane: 60 mM, and the pH adjusted with potassium salts to 7.2 (SAMADHI), Comparative experiments were also conducted on quartz substrates without employing the capillary device in a conventional dry box containing low moisture and was purged with medical grade nitrogen. Following desiccation, the cell samples were removed and membrane integrity was evaluated.

Quantification of Residual Moisture: Bulk gravimetric analysis of the water content of the samples was performed using a high precision analytical balance (Metler Toledo XP Ultra Microbalance, Columbus, Ohio). The initial and final sample weights were measured and used to calculate moisture content. Dry weights of samples were determined by baking in a vacuum oven at a temperature below the glass transition temperature of trehalose (~90° C.) for 8 h.

Viability Assessment: The membrane integrity was determined using Syto-13/ethydium bromide membrane integrity assays (Molecular Probes, Eugene, Oreg.). The stock solution for the Syto-13/ethydium bromide staining was prepared by adding 10 μL of 1 mg/mL Syto -13 solution (aq.) and 5 μL of 1.0 mg/mL solution ethydium bromide solution (aq.) to 8 mL of DMEM without phenol red or serum (Invitrogen Inc., Carlsbad, Calif.). After rehydration, 500 μL of Syto-13/ethydium bromide solution were added to the cells attached on coverslips, and the samples were incubated at 37° C. for 5 min. These samples were then imaged using an inverted microscope (Carl Zeiss Biosystems, Oberkochen, Germany) using FITC and PI filters. Cell viability was determined immediately after rehydration with this technique by counting the live (green) and dead (red) cells in seven representative images taken at different locations on the coverslip. Illustrative results are presented in FIG. 11.

2. Experiments with Mouse Oocyte:

Animals: Six-week-old B6D2F1 female mice were purchased from Charles River Laboratories (Boston, Mass., USA). All animal experiments were carried out with the approval of the animal care and use committee.

Retrieval of oocytes: The 6-week-old B6D2F1 female mice were superovulated with 7.5 IU of pregnant mare serum gonadotrophin (Sigma-Aldrich, St. Louis, Mo., USA) and 7.5 IU of human chorionic gonadotrophin (Sigma-Aldrich) given by intraperitoneal injections 48 h apart. Fourteen hours after human chorionic gonadotrophin injection, females were anaesthetized with avertin (Sigma-Aldrich) then killed by cervical dislocation and their oviducts were removed. The cumulus-oocyte-complex was released from the ampullary region of each oviduct by puncturing the oviduct with a 27-gauge needle. Cumulus cells were removed by exposure to hyaluronidase (80 IU/ml) (Irvine Scientific, Santa Ana, Calif., USA) for 3 min and washed three times with human tubal fluid (HTF) medium (Irvine Scientific) with 10% fetal bovine serum (FBS; Gibco, Carlsbad, Calif., USA). Oocytes were transferred and cultured in HTF medium (Quinn et al. 1995) containing 10% FBS at 37° C. and 5% $CO_2$ in air until they were vitrified by desiccation.

Desiccation: Desiccation experiments were performed employing the capillary device described in Example 1 above and following the same protocols.

3. Experiments with Insulin:

Materials and Methods: Chemically defined, recombinant from *Saccharomyces cerevisiae* human insulin solution with a concentration of 10 mg/mL was obtained from Sigma-Aldrich (St. Louis, Mo.) and stored at 4° C. High purity, low endotoxin trehalose dihydrate was obtained from Pfanstiehl (Cleveland, Ohio) and glyercol was acquired from Sigma-Aldrich. The insulin was serially diluted down to produce a stock solution of 25 µg/mL insulin concentration in Ultra-Pure™ distilled water and the solution was added to the previously vortexed trehalose-based solution. A separate insulin-based distilled water solution with no trehalose or glycerol was designated as the control group. Both experimental and control solutions were stored at 4° C. EMD Millipore (Billerica, Mass.) hydrophilic membrane with 0.22 µm pore size was used as the capillary substrate. All samples were placed within a vacuum chamber which was connected to an Edwards RV3 Two Stage Rotary Vane Pump (Crawley, United Kingdom) and Drierite desiccation column. The insulin-based samples were then continuously dried under vacuum for a duration of 25 minutes at a pressure between −27 and −30 in Hg. After drying, samples were removed and reweighed to determine the amount of water loss due to drying. The Moisture Residue Ratio ($gH_2O$/gdw) was calculated for all desiccated samples to quantify the efficiency of the desiccation procedure. After desiccation, all samples were rehydrated in 4× the amount of distilled water lost due as a result of drying. Concurrently, "undesiccated" samples of the trehalose-based insulin solution were rehydrated in distilled water to serve as a proteinious activity benchmark for the desiccated samples. The ELISA protocol provided by the supplier (Life Technologies) was followed after which the microtiter plate containing standards and all groups of samples were read and analyzed by the Epoch 2 Microplate Spectrometer (BioTek Instruments, Winooski, Vt.) with related Gen5 Data Analysis software that generates optical density (OD) readings signifying protein activity. Results are illustrated in FIG. 17.

While aspects of the invention have been illustrated and described, it is not intended that these aspects illustrate and describe all possible forms of the invention. Rather, the words used in the specification are words of description rather than limitation, and it is understood that various modifications and substitutions may be made thereto without departing from the spirit and scope of the invention.

| PATENT DOCUMENT REFERENCES | | |
| --- | --- | --- |
| 6,808,651 B1 | October 2004 | Katagiri, et al. |
| 7,883,664 B2 | February 2011 | G. Elliott; N. Chakraborty. |
| 8,349,252 B2 | January 2013 | G. Elliott; N. Chakraborty. |
| US 2013/0157250 A1 | June 2013 | Gutierrez et al. |
| US 2013/0260452 A1 | October 2013 | Toner et al. |

NON-PATENT REFERENCES

Chakraborty N, Menze M A, Malsam J, Aksan A, Hand S C, et al. (2011) Cryopreservation of Spin-Dried Mammalian Cells, PLoS ONE 6(9): e24916.

Chakraborty N, Biswas D, Elliott G D (2010) A Simple Mechanistic Way to Increase the Survival of Mammalian Cells During Processing for Dry Storage, Biopreservation and Biobanking, 8 (2), 107-114.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A non-cryogenic biological material vitrification device comprising:
    a) a receptacle comprising a first membrane and a second membrane, the first membrane, the second membrane, or both comprising a plurality of contiguous capillary channels each having a first opening and a second opening, the first membrane and said second membrane arranged so as to be able to contact a vitrification mixture when placed in the receptacle such that the first membrane contacts a first surface of the vitrification mixture and the second membrane contacts a second surface of the vitrification mixture such that the first opening of said capillary channels is operably in contact with said vitrification mixture; and
    b) an enclosure operably in fluidic communication with said second openings of the capillary channels to form an enclosure environment, said enclosure in fluidic communication with an external environment wherein a pressure, temperature, humidity, or combinations thereof within said enclosure environment can operably be controlled.

2. The device of claim 1, wherein an outside surface of said enclosure comprises one or more sealable inlets and one or more sealable outlets to facilitate gas flow and desiccation action.

3. The device according to claim 2, the sealable inlet(s) and outlet(s) enable flow of gas across or maintain reduced pressure across said second openings in order to enhance desiccation action.

4. The device according to claim 1, wherein said enclosure is impervious to moisture and gas.

5. The device of claim 1, further comprising one or more capillary pipes or capillary wicks operably in communication with said vitrification mixture and an enclosure environment in order to enhance desiccation action.

6. The device of claim 1, wherein said receptacle comprises multiple cavities comprising an inter cavity drying space.

7. The device of claim 1, wherein said device is configured as a wearable device.

8. The device according to claim 1, wherein said enclosure and said receptacle comprise material storable at a temperature between −196° C. to 60° C.

9. The device according to claim 1 wherein the first opening of said capillary channels in said first membrane are proximal and the first opening of said capillary channels in said second membrane, and the second opening of said capillary channels in said first membrane are opposite and the second opening of said capillary channels in said second membrane.

* * * * *